United States Patent
Yoon et al.

(10) Patent No.: US 11,494,147 B2
(45) Date of Patent: Nov. 8, 2022

(54) SENSING BENDING OF MULTIPLE JOINTS

(71) Applicant: Microsoft Technology Licensing, LLC, Redmond, WA (US)

(72) Inventors: Sang Ho Yoon, Redmond, WA (US); Siyuan Ma, Bothell, WA (US); James David Holbery, Bellevue, WA (US)

(73) Assignee: Microsoft Technology Licensing, LLC, Redmond, WA (US)

(*) Notice: Subject to any disclaimer, the term of this patent is extended or adjusted under 35 U.S.C. 154(b) by 718 days.

(21) Appl. No.: 16/453,885

(22) Filed: Jun. 26, 2019

(65) Prior Publication Data

US 2020/0404994 A1 Dec. 31, 2020

(51) Int. Cl.
*G06F 3/14* (2006.01)
*A61B 5/296* (2021.01)
*A41D 19/00* (2006.01)
*G06F 3/01* (2006.01)

(52) U.S. Cl.
CPC ............ *G06F 3/14* (2013.01); *A41D 19/0027* (2013.01); *A61B 5/296* (2021.01); *G06F 3/014* (2013.01)

(58) Field of Classification Search
CPC ................ A41D 19/0027; A61B 5/296; A61B 2560/0223; A61B 2562/0214; A61B 5/6806; A61B 5/1125; A61B 5/1121; G06F 3/014; G06F 3/017
See application file for complete search history.

(56) References Cited

U.S. PATENT DOCUMENTS

| | | | |
|---|---|---|---|
| 5,449,002 A | 9/1995 | Goldman | |
| 5,610,528 A | 3/1997 | Neely et al. | |
| 6,532,824 B1 | 3/2003 | Ueno et al. | |
| 7,302,858 B2 | 12/2007 | Walsh et al. | |
| 7,509,870 B2 | 3/2009 | Aebersold et al. | |
| 7,712,373 B2 | 5/2010 | Nagle et al. | |
| 2010/0249675 A1* | 9/2010 | Fujimoto | G06F 3/014 601/40 |

(Continued)

FOREIGN PATENT DOCUMENTS

| | | |
|---|---|---|
| CN | 102707853 A | 10/2012 |
| KR | 100905309 B1 | 7/2009 |

OTHER PUBLICATIONS

"International Search Repod and Written Opinion Issued in PCT Application No. PCT/US20/031974", dated Aug. 20, 2020, 12 Pages.

(Continued)

*Primary Examiner* — Alexander Eisen
*Assistant Examiner* — Kebede T Teshome
(74) *Attorney, Agent, or Firm* — Alleman Hall Creasman & Tuttle LLP (57) ABSTRACT

Examples are disclosed that relate to sensor devices configured to sense bending in multiple joints. One example provides a sensor device configured to span a first articulable joint and a second articulable joint. The sensor device comprises a plurality of electrodes arranged in a stack and connected to a base. The plurality of electrodes comprise a first electrode arranged at a first joint region of the sensor device that is configured to be positioned at the first articulable joint, a second electrode arranged at a second joint region of the sensor device that is configured to be positioned at the second articulable joint, and a reference electrode.

16 Claims, 7 Drawing Sheets

(56) References Cited

U.S. PATENT DOCUMENTS

2015/0141784 A1* 5/2015 Morun .................... G06F 3/014
427/79
2017/0168567 A1* 6/2017 Reese ..................... G06F 3/016
2018/0116559 A1 5/2018 Otaka et al.

OTHER PUBLICATIONS

Shen, et al., "A Soft Stretchable Bending Sensor and Data Glove Applications", In Journal of Robotics and Biomimetics, vol. 3, Issue 1, Dec. 1, 2016, pp. 1-8.

* cited by examiner

SENSING BENDING OF MULTIPLE JOINTS

BACKGROUND

Many types of devices may be configured to bend at multiple locations along a device length. For example, a wearable device used to interact with virtual objects rendered on a display (e.g. a glove device) may include multiple bendable or movable joints that correspond with the locations of human joints (e.g. finger joints).

SUMMARY

Examples are disclosed that relate to sensor devices configured to sense bending at multiple locations. One example provides a sensor device configured to span a first articulable joint and a second articulable joint. The sensor device comprises a plurality of electrodes arranged in a stack and connected to a base. The plurality of electrodes comprise a first electrode arranged at a first joint region of the sensor device that is configured to be positioned at the first articulable joint, a second electrode arranged at a second joint region of the sensor device that is configured to be positioned at the second articulable joint, and a reference electrode.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

A wearable device may be used to interact with virtual objects rendered on a display. Interaction between the wearable device and a virtual object may take different forms—for example, the wearable device may function as an output device that provides haptic and/or force feedback in response to contact between the wearable device and the virtual object. Alternatively or additionally, the wearable device may function as an input device, where a sensed position and/or movement of the wearable device is used to vary displayed aspects of the virtual object. As examples, contact between the wearable device and the virtual object may prompt the application of a virtual force to the virtual object, compression of the virtual object, and other changes to the state of the virtual object.

However, detecting the position and orientation of each individual moveable portion of the wearable device to provide for such interactions may pose challenges. For wearable devices that take the form of a glove, detecting the position and orientation of each moveable portion may be particularly challenging due to the complex motion of human hands. One potential approach may be to use an image sensor to monitor the wearable device and thereby use machine vision techniques to detect the position in space of each moveable portion of the device. However, conditions such as occlusion (e.g. of fingers by other portions of a hand) and inaccurate color detection (e.g. an inability to track black colors via infrared sensor) may interrupt image-based detection and introduce discontinuities in interactions with virtual objects, which may impact an immersive experience. Other approaches may arrange inertial motion sensors at different locations along a wearable device. However, for an object capable of movement of multiple independent joints (e.g. a human hand), the detection of motion and/or position of each independently movable portion of the object may utilize a relatively large number of motion sensors. This may increase device cost and a complexity of processing sensor data (e.g. including motion sensor calibration, accounting for magnetic influence on sensor output).

In view of the above, examples are disclosed that relate to sensor devices for sensing articulation at multiple locations, such as multiple articulable joints of a human body part. As described in more detail below, the disclosed examples include multiple electrodes each configured to produce output indicative of articulation at a respective sensing region relative to a common reference electrode. By comparing the output from each electrode to the common reference electrode, a bend angle at each corresponding sensing region (e.g. at each joint of a finger) may be determined. The disclosed examples also may facilitate the correction of a bend signal for contributions from elongation and pressure. Bend angles thus determined may then be used, for example, as input to mixed reality applications, virtual reality applications, and any other suitable application in which a bend angle of each of plural articulable locations may be used as feedback or input. Where the sensor device is implemented in a wearable glove, for example, sensed joint angles may be used to determine a representation of a wearer's hand and simulate interactions between the hand and virtual objects.

Figure 1:
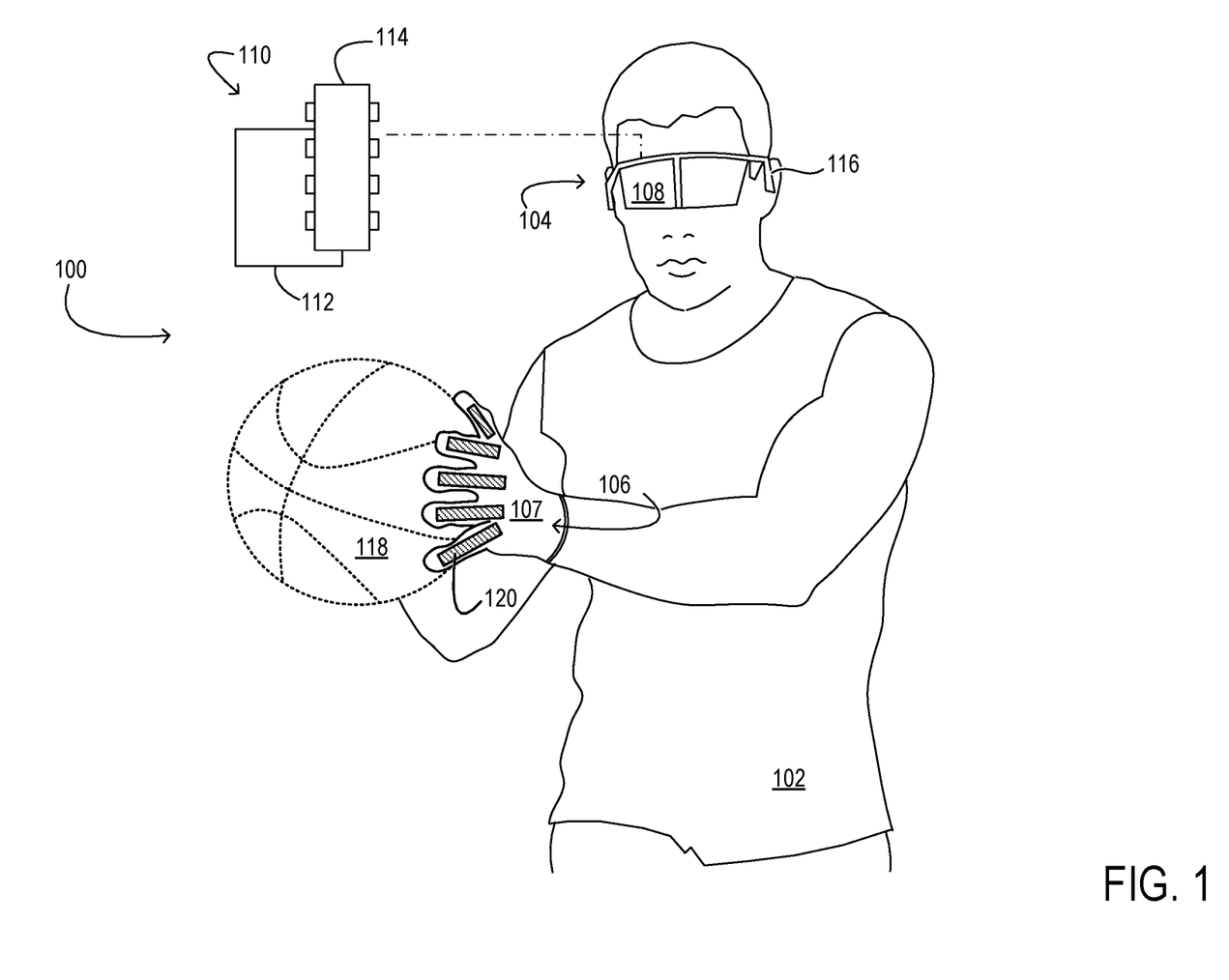
FIG. 1 shows aspects of an example display system configured to present a mixed reality experience to a user.

FIG. 1 shows aspects of an example display system 100 configured to present a mixed reality experience to a user 102. Display system 100 is illustrated as being used to support gameplay, but may be used in any other suitable scenario. Display system 100 includes a head-mounted display (HMD) device 104 and a wearable device 106, shown in the form of a glove, configured to sense articulation of one or more of the articulable joints (e.g., knuckles) in a hand 107 of user 102. HMD device 104 includes a near-eye display 108 configured to display virtual imagery in the field of view of user 102. In some examples, near-eye display 108 is a see-through display, enabling real-world and virtual imagery to be admixed in the user's field of view. In other examples, the near-eye display 108 is opaque, providing a fully immersive virtual reality experience. In HMD device 104, signals encoding virtual imagery are sent to display 108 via an on-board computing device 110. Computing device 110 includes a suitable logic device 112 (e.g., a processor) and associated memory 114. HMD device 104 further may include loudspeakers 116 to allow user 102 to experience immersive audio.

Leveraging communications componentry arranged in HMD device 104, computing device 110 may be communicatively coupled to one or more off-board computing devices via a network. Thus, the virtual imagery that user 102 sees may, in some examples, be composed and/or rendered by an off-board computing device and sent wirelessly to computing device 110. In other examples, the virtual imagery may be composed and rendered on-board.

Wearable device 106 is configured to augment the mixed reality experience presented by HMD device 104 by providing output representing articulation of hand 107 of user 102. The articulation sensed via wearable device 106 may be used to vary the state of virtual objects rendered within the mixed realty experience. In the mixed reality example shown in FIG. 1, HMD device 104 determines that the articulation of hand 107 represents an intention by user 102 to grip a virtual basketball 118 rendered within the mixed reality experience. Accordingly, virtual basketball 118 is rendered in a position constrained by the grip formed by hand 107. HMD device 104 may update the position of virtual basketball 118 as the orientation and position of hand 107 changes to simulate the virtual basketball with realistic physical behavior. As another example, in a virtual reality implementation, the output from wearable device 106 may be used to render a virtual model of hand 107 (and optionally to render a virtual object based on the pose of the virtual hand model), to detect gestures performed by the hand, and to determine forces to be applied to virtual objects in response to articulation of the hand. While shown in the form a glove, a wearable device take other forms in other examples, such as a sleeve worn around an arm, a leg, foot, and/or another body part of user 102.

Figure 2:
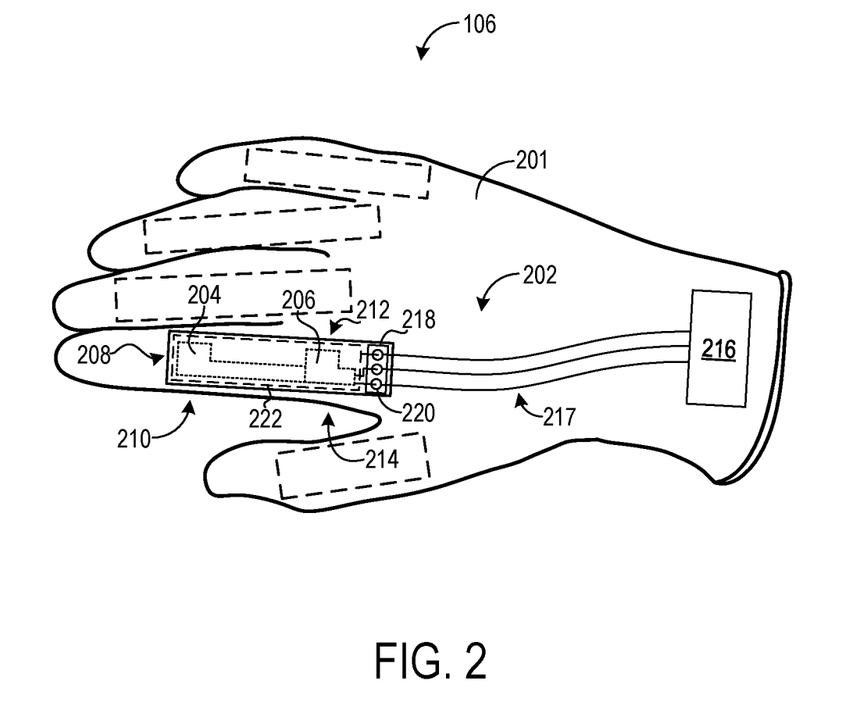
FIG. 2 shows an example wearable device comprising a sensor device configured to sense bend angles of each of a plurality of joints.

Wearable device 106 includes at least one sensor device 120 configured to sense articulation of multiple articulable joints of hand 107 (a sensor device is shown for each finger in FIG. 1). FIG. 2 shows wearable device 106 in more detail. Wearable device 106 includes a body 201 (e.g. a fabric portion configured to fit a hand) and a plurality of sensor devices, one or more of which include electrodes that are configured to span multiple articulable joints of a hand wearing the wearable device. In some examples, the sensor devices may be contained between an inner and outer layer of fabric, while in other examples, the sensor devices may be contained within a housing that is not concealed by an outer layer of fabric.

One sensor device 202 is shown in schematic detail. To sense articulation of the articulable joints, the sensor device 202 includes a first electrode 204 and a second electrode 206. First electrode 204 comprises a sensing portion arranged at a first joint region 208 of sensor device 202, where the first joint region is configured to be positioned at a first articulable joint (schematically indicated at 210) of the hand when wearable device 106 is worn. Second electrode 206 comprises a sensing portion arranged at a second joint region 212 of sensor device 202, where the second joint region is configured to be positioned at a second articulable joint (schematically indicated at 214) of the hand when wearable device 106 is worn.

Sensor device 202 further includes a controller 216 configured to determine respective bend angles of the sensor device at first and second joint regions 208 and 212, and a base 218 to which each electrode is attached. The base 218 provides mechanical support for electrodes 202, 204 and 206, and also comprises electrical connectors (e.g., connector 220) for connecting first and second electrodes 204 and 206, and also a reference electrode 222, to controller 216 via conductors 217 (e.g. wires or traces). Controller 216 is configured to receive a first signal from first electrode 204, a second signal from second electrode 206, and also a reference signal from reference electrode 222. As described in further detail below, controller 216 may determine a first bend angle of sensor device 202 at first joint region 208 based on the first signal and the reference signal, and a second bend angle of the sensor device at second joint region 212 based on the second signal and the reference signal.

While shown as being configured to span two articulable joints of a finger, a sensor device according to the present disclosure may be configured to span, and thereby detect bending of, any suitable number of articulable joints, such as all of the articulable joints of a finger, and/or articulable joints of different fingers. In such examples, a respective sensing electrode may be provided for each articulable joint (or other location of interest), while a common reference electrode may be provided for all electrodes. This may allow up to all of the articulable joints of the hand to be sensed via a common sensing structure, reducing cost, sensor device footprint, and sensing complexity.

Figure 3:
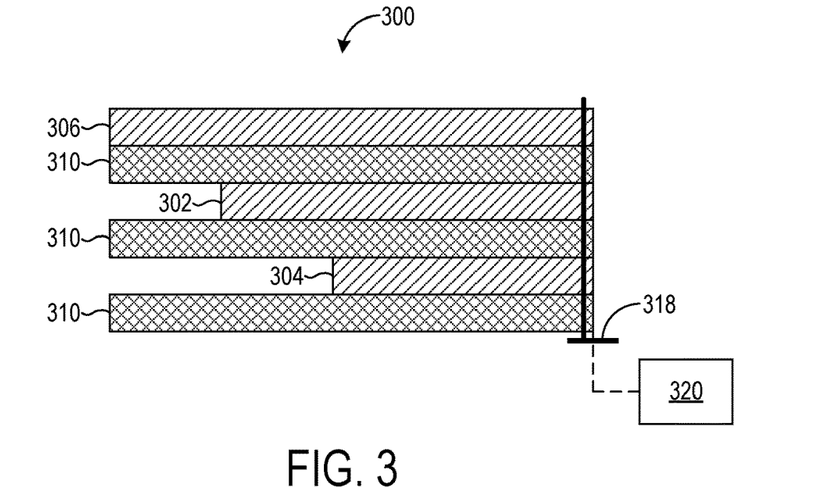
FIG. 3 shows a cross-sectional view of an example electrode stack for a sensor device.
Figure 4:
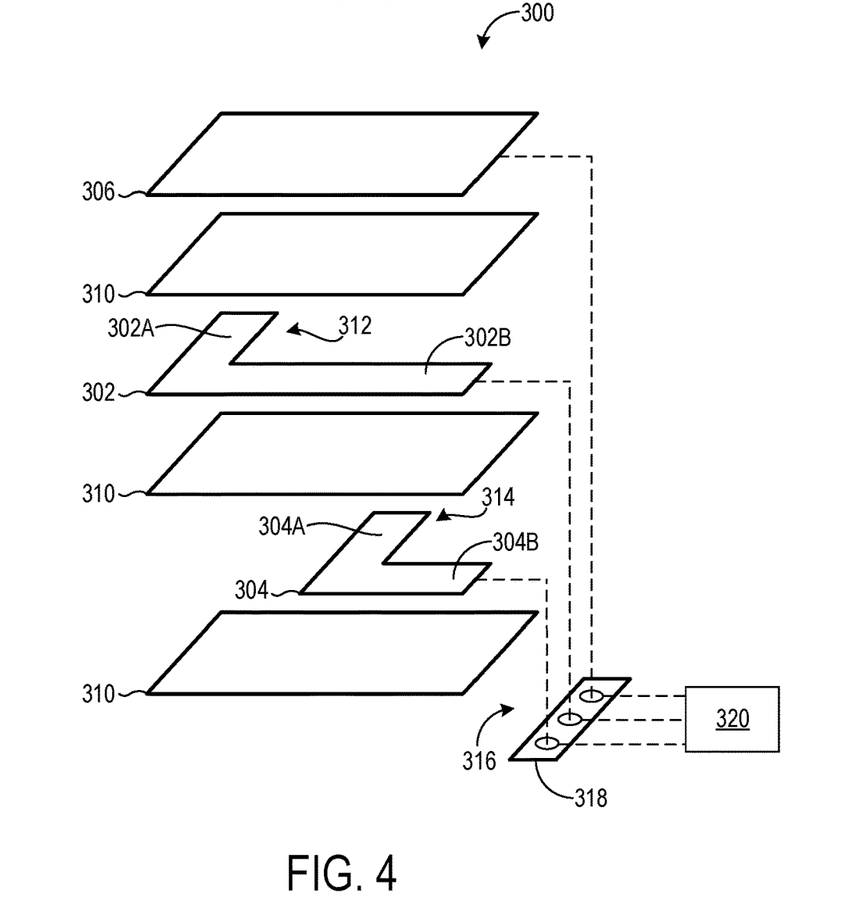
FIG. 4 shows an exploded view of the example electrode stack of FIG. 3.

FIG. 3 shows a schematic cross-sectional view of an example electrode stack 300 for a sensor device, and FIG. 4 shows an exploded view of electrode stack 300. Aspects of electrode stack 300 may be implemented by sensor device 202, for example.

Electrode stack 300 includes a first electrode 302 and a second electrode 304 arranged on the same side of a reference electrode 306. Electrode stack 300 also includes a plurality of dielectric layers 308 interleaved with the electrodes to physically separate and electrically insulate each electrode from adjacent electrodes. Electrodes 302, 304, 306 and dielectric layers 308 are configured to be flexible (and in some examples soft), such that upon bending of the electrode stack 300 (e.g. as the joint being sensed bends), the electrodes and dielectric layers flex with the joint. This may allow electrode stack 300 to bend throughout a wide range of bend radii. In some examples, dielectric layers 308 each may comprise a dielectric coating formed on each electrode, while in other examples the dielectric layers may be independent from the electrode layers (which may still be coated with an insulating material). Electrodes 302, 304, and 306 may be made from any suitable material, including but not limited to metallic films (e.g. aluminum) on a flexible substrate, and polymer(s) (e.g. silicone) mixed with conductive materials (e.g. carbon powder, carbon nanotubes, metal fillers). Likewise, dielectric layers 308 also may be made from any suitable material. Examples include ceramic/polymer composite materials (e.g. a polyurethane matrix comprising barium titanate powder) and other insulating materials such as polyurethane, silicone, and acrylate.

When driven by a suitable signal source, a capacitance of the first electrode 302 and a capacitance of the second electrode 304, may be sensed relative to the reference electrode 306. Upon a change in a joint angle sensed by electrode stack 300, the capacitances of the electrodes change. The changes in capacitance may be sensed to determine a first bend angle at a first joint region 312 where the first electrode is arranged, and a second bend angle at a second joint region 314 where the second electrode is arranged, thereby allowing the bend angles of these articulable joints to be individually determined.

As shown in FIG. 4, first and second electrodes 302 and 304 are at least partially offset. More particularly a sensing portion 302A of first electrode 302 is offset from a sensing portion 304A of second electrode (e.g. in the thickness direction). Conversely, a stem portion 302B of first electrode 302 may at least partially overlap a stem portion 304B of second electrode 304. With the sensing portions positioned over respectively different articulable joints, bending at first joint region 312 can be localized and distinguished from bending at second joint regions 314. In other examples, the stem portions of the first electrode and second electrode may have no overlap, or a different degree of overlap than shown in FIG. 4 (e.g. the stem portions may be both vertically offset in a thickness direction and laterally offset across a width of the electrode stack). While first electrode 302 and second electrode 304 each have a polygonal shape with an approximately ninety-degree angle between the stem portion and sensing portion, the electrodes may have any other suitable shape in other examples.

The electrodes are connected to respective connectors 316 arranged on base 318. Connectors 316, in turn, are coupled to a controller 320 (e.g. controller 216 of FIG. 2) via conductors (e.g. wires or traces). Controller 320 is configured to determine a first bend angle of electrode stack 300 at first joint region 312 based on signals read from first electrode 302 and reference electrode 306. Likewise, controller 320 is configured to determine a second bend angle of electrode stack 300 at second joint region 314 based on signals read from second electrode 304 and reference electrode 306.

Controller 302 also may be configured to apply respective correction terms for the first bend angle and the second bend angle, where the respective correction terms correct at least partially for any capacitance changes arising from stretching of electrode stack 300 and any pressure applied to a surface of the stack. This may help to achieve an accurate measurement of bending at first and second joint regions 312 and 314 without contributions to measurements from non-bending sources.

One example of a method of determining bend angles from capacitance measurements and applying corrective terms is as follows. A first bend angle $\theta_1$ at first joint region 312 may be determined by $\theta_1=(C_R-C_1*\beta_0/C_R*\alpha_1$, where $C_R$ is the measured capacitance at reference electrode 306, $C_1$ is the measured capacitance at first electrode 302, $\beta_1$ is a coefficient correcting $\theta_1$ for elongation and/or pressure, and $\alpha_1$ is a coefficient for converting the capacitive measurements for the first joint region to an angle. A second bend angle $\theta_2$ at second joint region 314 may be determined as $\theta_2=(C_R-C_2*\beta_2)/C_R*\alpha_2$, where $C_R$ is the measured capacitance at reference electrode 306, $C_2$ is the measured capacitance at second electrode 304, $\beta_2$ is a coefficient correcting $\theta_2$ for elongation and/or pressure, and $\alpha_2$ is a coefficient for converting the capacitive measurements for the second joint region to an angle.

The terms $\beta_1$, $\beta_2$, $\alpha_1$, and $\alpha_2$ may be determined in any suitable manner. For example, the $\alpha_1$ and $\alpha_2$ terms may be determined by associating capacitance values with ground truth measurements of corresponding bend angles as measured by optical imaging, an external bend measurement tool, or other suitable manner. The $\beta_1$ and $\beta_2$ correction terms may be determined by observing changes in capacitance values as each electrode undergoes elongation (e.g. without bending). These terms may be specific to an electrode geometry, such that these terms may be redetermined if an alternative electrode geometry is employed. A look-up table may be used to implement these terms in some examples. In other examples, any other suitable mechanism may be used to implement these terms.

Figure 5:
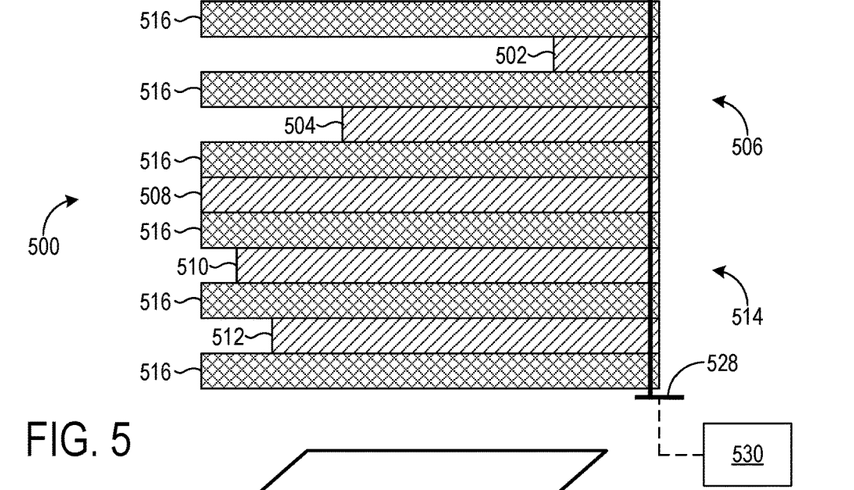
FIG. 5 shows a cross-sectional view of another example electrode stack for a sensor device.
Figure 6:
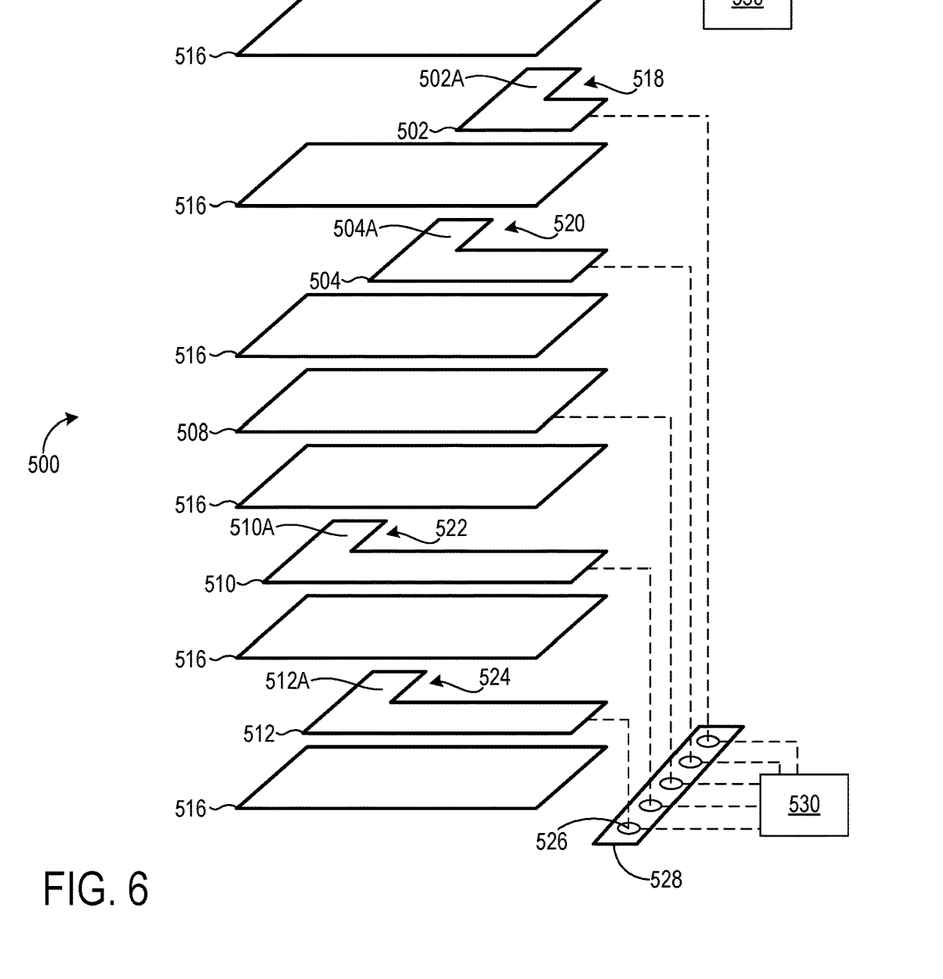
FIG. 6 shows an exploded view of the electrode stack of FIG. 5.

FIG. 5 shows a cross-sectional view of another example electrode stack 500, and FIG. 6 shows an exploded view of electrode stack 500. Aspects of electrode stack 500 may be implemented by sensor device 202 (FIG. 2), for example. Electrode stack 500 includes a first electrode 502 and a second electrode 504 arranged on a first side 506 of a reference electrode 508, and a third electrode 510 and a fourth electrode 512 arranged on a second side 514 of reference electrode 508 opposite first side 506. Further, plural dielectric layers 516 are schematically illustrated as interleaved with the electrodes.

When driven by a suitable signal source, the capacitance of each electrode relative to reference electrode 508 may be sensed. Upon bending of electrode stack 500, the capacitances change. Thus, the change in the capacitance of first electrode 502 relative to reference electrode 508 can be sensed to determine a first bend angle of electrode stack 500 at a first joint region 518 where the first electrode is arranged, a change in the capacitance of second electrode 504 can be sensed to determine a second bend angle of the electrode stack at a second joint region 520 where the second electrode is arranged, a change in the capacitance of third electrode 510 can be sensed to determine a third bend angle of the electrode stack at a third joint region 522 where the third electrode is arranged, and a change in the capacitance of fourth electrode 512 can be sensed to determine a fourth bend angle of the electrode stack at a fourth joint region 524 where the fourth electrode is arranged.

The electrodes are each connected to respective connectors (e.g. connector 526) arranged on a base 528. Connectors 526 are coupled via conductors (e.g. traces or wires) to a controller 530 (e.g. controller 216 of FIG. 2) configured to receive values representing the respective capacitances formed on each of the electrodes. In determining respective bend angles at joint regions 518, 520, 522, and 524, controller 530 may apply respective correction terms for the bend angles, where the respective correction terms correct at least partially for elongation of electrode stack 500 and/or any pressure applied to a surface of the stack.

In some examples, controller 530 may compare a signal from a sensing electrode (first electrode 502 or second electrode 504) on first side 506 of reference electrode 508 to a signal from a sensing electrode (third electrode 508 or fourth electrode 510) on second side 514 of the reference electrode to determine a direction in which an articulable joint is bent. Where the articulable joint is a knuckle of a human digit, for example, such comparison may allow a determination as to whether the digit is in a state of flexion or elongation, e.g. based upon a sign of a computed bend angle using the equations for $\theta_1$ and $\theta_2$ above.

In some examples, controller 530 may execute a calibration procedure using signals received from electrode stack 500. The calibration procedure may enable a sensor device (e.g. sensor device 202 of FIG. 2) in which the electrode stack is implemented to accurately and repeatably sense bend angles while accounting for variations in angle sensing due to the variations in the appendage (e.g. finger size) or object the sensor device is attached to, and variations due to the fit of the sensor device (and potentially the fit of a wearable device implementing the sensor device) on the appendage or object. In this calibration procedure, controller 530 may collect capacitance readings from each electrode in electrode stack 500, and based on the readings, define a neutral plane location corresponding to a capacitance reading that exhibits no change, or less than a threshold change, upon bending. In some examples, the neutral plane location may correspond to a location at reference electrode 508. Controller 530 may then calculate and predict the relationship between capacitance reading and bend angle for each sensor device from which readings are received, based on comparing capacitance readings to the neutral plane location.

As compared to electrode stack 300 of FIG. 3, electrode stack 500 provides for the sensing of bend angles at a greater number of joint regions using a common sensing structure. Arranging reference electrode 508 between sensing electrodes above and below the reference electrode may allow the sensing of a greater number of joints than positioning all electrodes on a same side of the reference electrode, as such an arrangement may reduce a distance between the reference electrode and a farthest sensing electrode in an electrode stack, and thereby support the formation of sufficiently strong electric fields to allow the reception of capacitive signals from the sensing electrodes with sufficient signal-to-noise ratios even when relatively higher numbers of electrodes are included.

Figure 7:
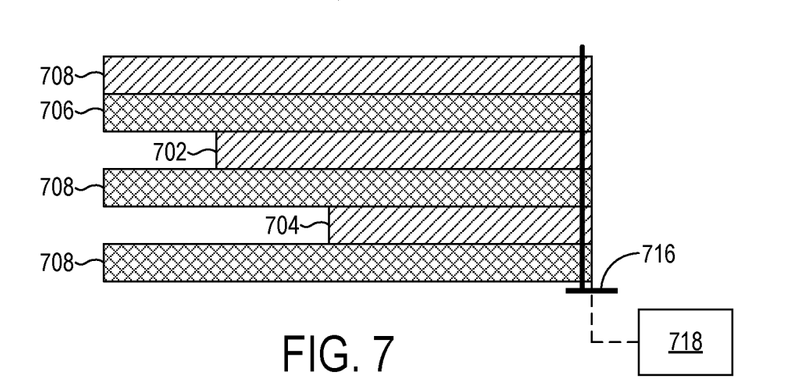
FIG. 7 shows a cross-sectional view of another example electrode stack for a sensor device.
Figure 8:
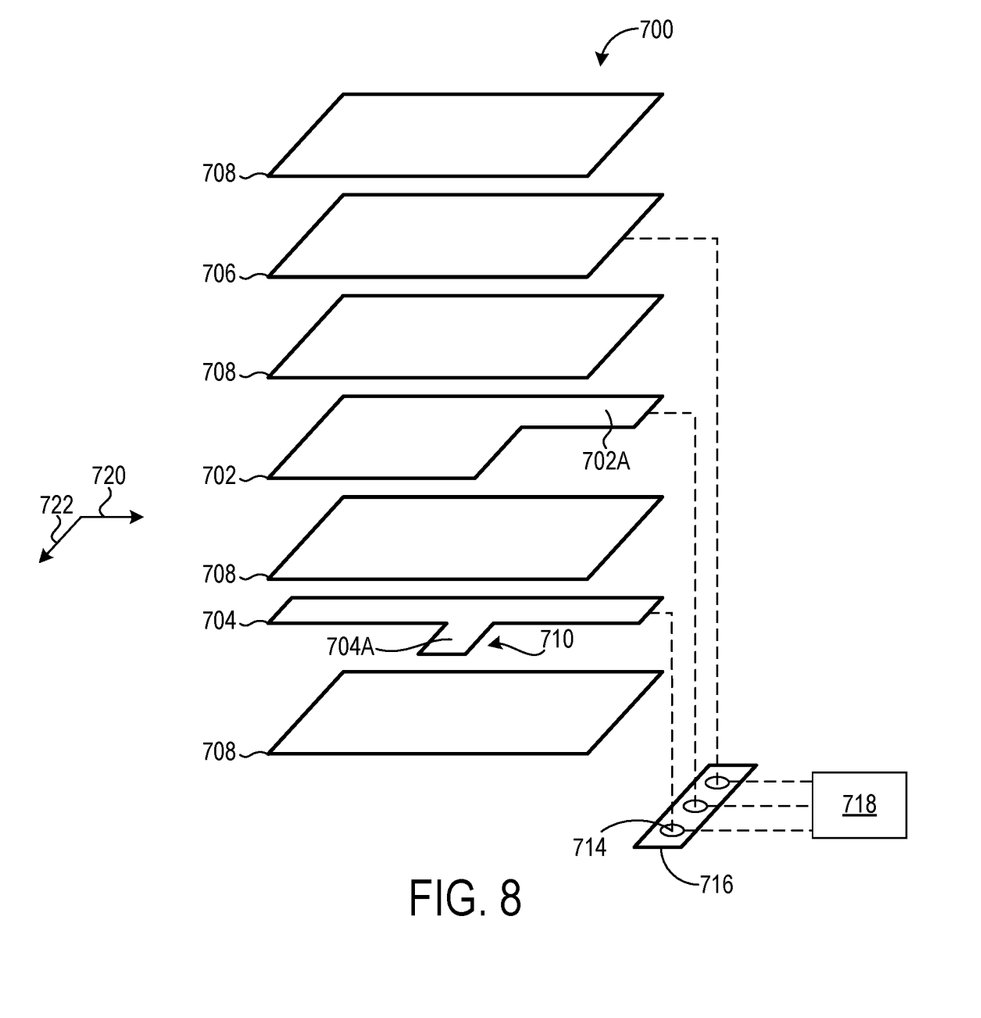
FIG. 8 shows an exploded view of the electrode stack of FIG. 7.

FIG. 7 shows a cross-sectional view of another example electrode stack 700 that may be used to sense bending at multiple regions, and FIG. 8 shows an exploded view of electrode stack 700. Aspects of stack 700 may be implemented by sensor device 202 (FIG. 2), for example. Electrode stack 700 includes a first electrode 702 and a second electrode 704 arranged on the same side (e.g. below in a thickness direction) of a reference electrode 706. Stack 700 also includes a plurality of dielectric layers 708 interleaved with the electrodes. In other examples, electrodes 702, 704 may be arranged on opposite sides of the reference electrode 706. In some examples, dielectric layers 708 may comprise a plurality of discrete layers, while in other examples the layers may comprise a dielectric coating formed on each electrode, as described above. The electrodes are attached to a base 716 comprising connectors (e.g. connector 714) for connecting the electrodes to a controller 718. Controller 718 may determine a first bend angle of a joint region 710 along a first axis 720, and a second bend angle of the joint region 710 along a second axis 722. In some examples, first axis 720 may be perpendicular to second axis 722, while in other examples the axes may have any other suitable geometric relationship.

The sensing of bend angles along perpendicular axes may be facilitated by orienting sensing portion 702A and sensing portion 704A along the perpendicular axes 720 and 722, for example. In the depicted examples, both first and second joint regions 702A and 704A are arranged over a common articulable joint, such that bending of the joint can be sensed in both axes 720 and 722. Where the articulable joint is a knuckle of a human thumb, for example, bending of the thumb along a yaw axis can be detected and distinguished from detected bending of the thumb along a pitch axis. In other examples, a pair of electrodes analogous to first and second electrodes 702 and 704 may be provided for each of a plurality of articulable joints to enable the sensing of bend angles of each along different axes. Further, controller 718 may apply respective correction terms for the bend angles, where the respective correction terms correct at least partially for elongation of electrode stack 700 and a pressure applied to a surface of the stack.

Figure 9:
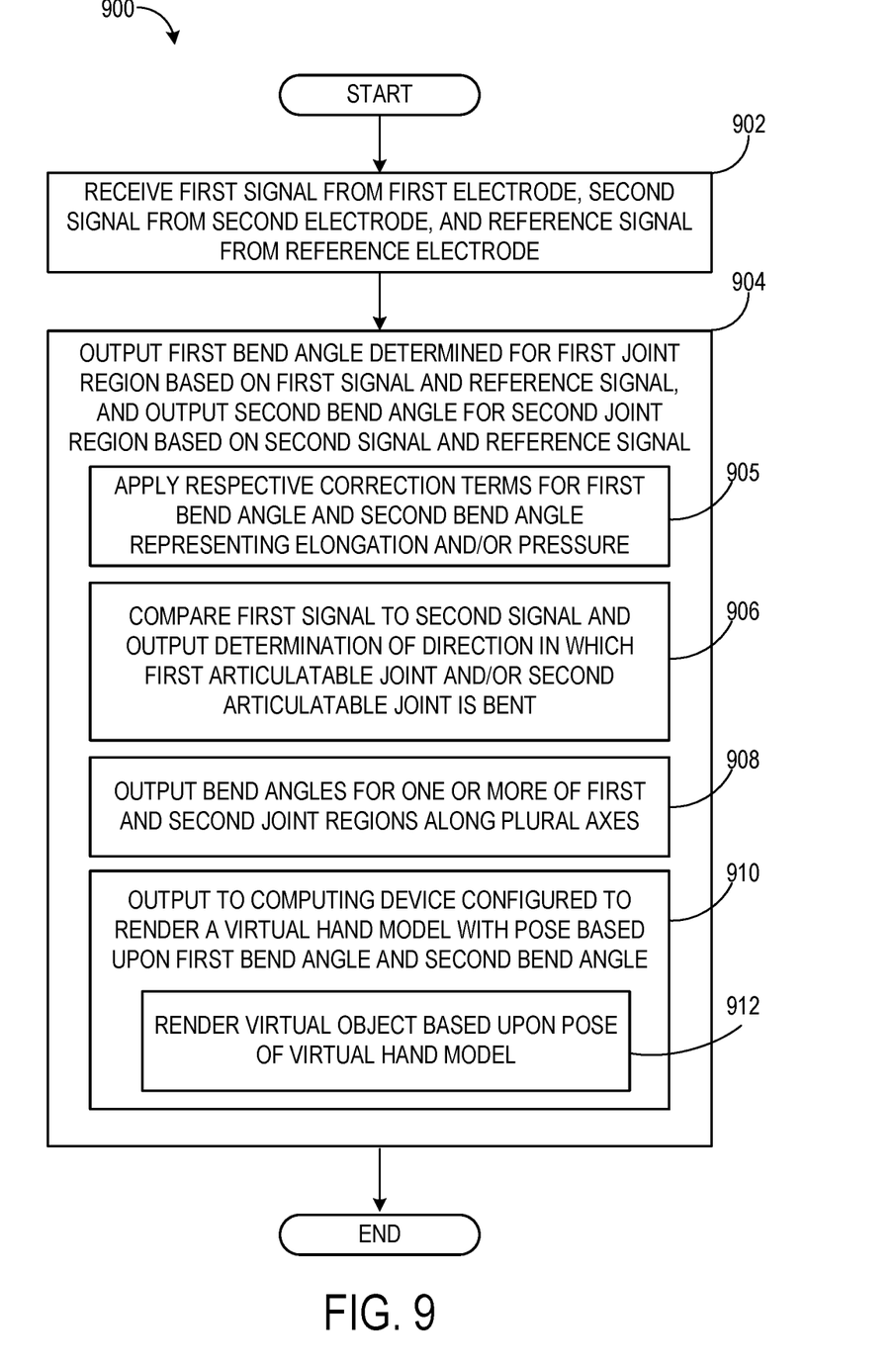
FIG. 9 shows a flowchart illustrating a method of determining bend angles at a sensor device comprising a plurality of electrodes.

FIG. 9 shows a flowchart illustrating a method 900 of determining bend angles at a sensor device comprising a plurality of electrodes. Method 900 may be implemented using sensor device 202 via stacks 300, 500, and/or 700, as examples.

At 902, method 900 includes receiving a first signal from a first electrode of the plurality of electrodes, a second signal from a second electrode of the plurality of electrodes, and a reference signal from a reference electrode of the plurality of electrodes. At 904, method 900 includes determining and outputting a first bend angle of the sensor device for the first joint region based on the first signal and the reference signal, and determining and outputting a second bend angle for a second joint region based upon the second signal and reference signal.

In some examples, as indicated at 905, method 900 may include applying respective correction terms for the first bend angle and the second bend angle, each of the respective correction terms at least partially correcting for one or both of an elongation of the sensor device and a pressure applied to a surface of the sensor device. As described above, the correction terms may be determined by observing changes in capacitance values as each electrode undergoes elongation (e.g. without bending). The correction terms may be specific to an electrode geometry, such that the correction terms may be redetermined if an alternative electrode geometry is employed. A look-up table may be used to implement the correction terms, for example. In other examples, any other suitable mechanism may be used to implement the correction terms. Further, in some examples, as shown at 906, the first signal may be compared to the second signal to determine a direction in which one or more of the first articulable joint and the second articulable joint is bent. Additionally, in some examples, bend angles may be determined for one or more of the first and second joint regions along plural axes (e.g. perpendicular axes).

The determined angles may be output to any suitable device. In some examples, as indicated at 910, the angles may be output to a computing device configured to render a virtual hand model with a displayed pose based upon the first and second bend angles determined. Further, in some examples, a virtual object may be rendered based upon the pose of the virtual hand model (e.g. to display the virtual object as gripped, squeezed, etc.).

Various modifications to the sensor devices and stacks described herein are possible. As described above, the sensing structures described herein can be scaled to provide a common sensing structure capable of sensing bending at a plurality of different articulable joints. Further, implementations are possible in which sensor devices and stacks are configured to sense bend angles based on resistance measurements (e.g. using a material comprising a resistance that varies with bend angle, such as a polymer film containing a dispersion of silver nanowires, graphite, etc.). In such implementations, the resistance of each electrode may be measured to determine a bend angle at a joint region associated with that electrode. A controller configured to obtain measurements of the resistances of the electrodes may apply correction terms to the measurements to correct for drift (e.g. induced by temperature changes) and/or hysteresis. Further, the correction terms may vary as a function of the direction in which bending occurs.

A bend sensor according to the present disclosure may be used in any suitable application. For example, as described above, a virtual hand model may be rendered with a pose based on bend angles sensed by a sensor device. Further, a virtual object may be rendered based on the pose of the virtual hand model, e.g. to display deformation from pressure. Sensed bend angles and bending motions also may be used to determine a user's intended hand motion, e.g. to determine whether to display a virtual object as gripped, or to display a collision interaction with the virtual object. In other examples, a sensor device may be used to determine bend angles associated with the human body for medical rehabilitation, exercise, and training—e.g., to measure a human subject's response to stimuli or range of motion.

Further, a sensor device according to the present disclosure may be used in other applications than wearable devices. For example, a robotic device (e.g. a soft robotic device) may utilize a sensor device according to the present disclosure to determine bend angles associated with an appendage (e.g. a robot hand) of the robotic device, e.g. for use as a feedback signal in controlling the position and/or orientation of the appendage. Another example device that may employ a sensor device as disclosed includes a foldable device with one or more hinges.

In yet other examples, a sensor device may be used to determine bend angles with an articulating device inserted into plumbing, earthed tunnels, and other extended passages—e.g. in waste management, oil, gas, or plumbing contexts. In these examples, other mechanisms of sensing bend angles of an articulating device, such as optical imaging, may be significantly more cumbersome and ineffective than employing the disclosed sensor devices.

In some embodiments, the methods and processes described herein may be tied to a computing system of one or more computing devices. In particular, such methods and processes may be implemented as a computer-application program or service, an application-programming interface (API), a library, and/or other computer-program product.

Figure 10:
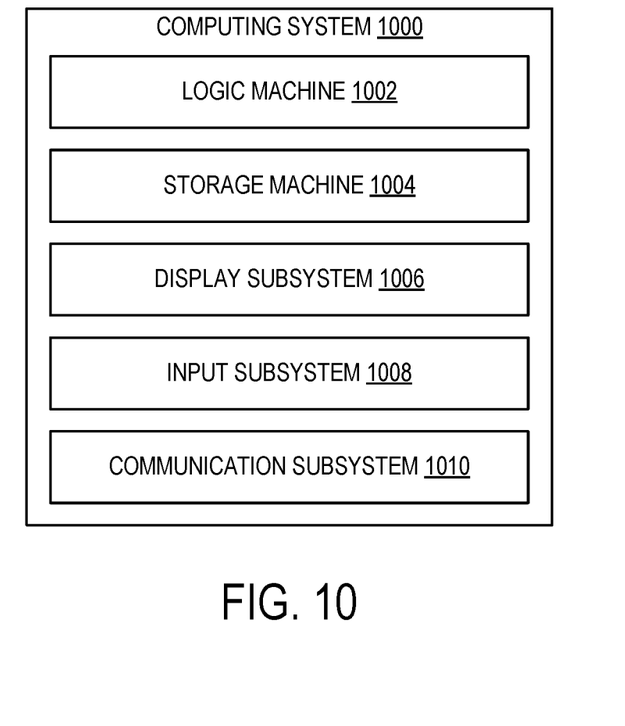
FIG. 10 shows a block diagram of an example computing device.

FIG. 10 schematically shows a non-limiting embodiment of a computing system 1000 that can enact one or more of the methods and processes described above. Computing system 1000 is shown in simplified form. Computing system 1000 may take the form of one or more personal computers, server computers, tablet computers, home-entertainment computers, network computing devices, gaming devices, mobile computing devices, mobile communication devices (e.g. smart phone), and/or other computing devices.

Computing system 1000 includes a logic machine 1002 and a storage machine 1004. Computing system 1000 may optionally include a display subsystem 1006, input subsystem 1008, communication subsystem 1010, and/or other components not shown in FIG. 10.

Logic machine 1002 includes one or more physical devices configured to execute instructions. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic machine may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of the logic machine optionally may be distributed among two or more separate devices, which may be remotely located and/or configured for coordinated processing. Aspects of the logic machine may be virtualized and executed by remotely accessible, networked computing devices configured in a cloud-computing configuration.

Storage machine 1004 includes one or more physical devices configured to hold instructions executable by the logic machine to implement the methods and processes described herein. When such methods and processes are implemented, the state of storage machine 1004 may be transformed—e.g. to hold different data.

Storage machine 1004 may include removable and/or built-in devices. Storage machine 1004 may include optical memory (e.g. CD, DVD, HD-DVD, Blu-Ray Disc, etc.), semiconductor memory (e.g. RAM, EPROM, EEPROM, etc.), and/or magnetic memory (e.g. hard-disk drive, floppy-disk drive, tape drive, MRAM, etc.), among others. Storage machine 1004 may include volatile, nonvolatile, dynamic, static, read/write, read-only, random-access, sequential-access, location-addressable, file-addressable, and/or content-addressable devices.

It will be appreciated that storage machine 1004 includes one or more physical devices. However, aspects of the instructions described herein alternatively may be propagated by a communication medium (e.g. an electromagnetic signal, an optical signal, etc.) that is not held by a physical device for a finite duration.

Aspects of logic machine 1002 and storage machine 1004 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 1000 implemented to perform a particular function. In some cases, a module, program, or engine may be instantiated via logic machine 1002 executing instructions held by storage machine 1004. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

It will be appreciated that a "service", as used herein, is an application program executable across multiple user sessions. A service may be available to one or more system components, programs, and/or other services. In some implementations, a service may run on one or more server-computing devices.

When included, display subsystem 1006 may be used to present a visual representation of data held by storage machine 1004. This visual representation may take the form of a graphical user interface (GUI). As the herein described methods and processes change the data held by the storage machine, and thus transform the state of the storage machine, the state of display subsystem 1006 may likewise be transformed to visually represent changes in the underlying data. Display subsystem 1006 may include one or more display devices utilizing virtually any type of technology. Such display devices may be combined with logic machine 1002 and/or storage machine 1004 in a shared enclosure, or such display devices may be peripheral display devices.

When included, input subsystem 1008 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 1010 may be configured to communicatively couple computing system 1000 with one or more other computing devices. Communication subsystem 1010 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 1000 to send and/or receive messages to and/or from other devices via a network such as the Internet.

Another example provides a sensor device configured to span a first articulable joint and a second articulable joint, the sensor device comprising a plurality of electrodes arranged in a stack and connected to a base, the plurality of electrodes comprising a first electrode arranged at a first joint region of the sensor device that is configured to be positioned at the first articulable joint, a second electrode arranged at a second joint region of the sensor device that is configured to be positioned at the second articulable joint, and a reference electrode. In such an example, the sensor device may comprise a controller configured to receive a first signal from the first electrode, a second signal from the second electrode, and a reference signal from the reference electrode, output a first bend angle of the sensor device for the first joint region based on the first signal and the reference signal, and output a second bend angle of the sensor device for the second joint region based on the second signal and the reference signal. In such an example, the controller may be configured to apply respective correction terms for the first bend angle and the second bend angle, each of the respective correction terms correcting at least partially for one or both of an elongation of the sensor device and a pressure applied to a surface of the sensor device. In such an example, the base may comprise electrical connectors for connecting the first electrode, the second electrode, and the reference electrode to the controller. In such an example, the controller alternatively or additionally may be configured to compare the first signal to the second signal and output a determination of a direction in which one or more of the first articulable joint and the second articulable joint is bent. In such an example, the controller alternatively or additionally may be configured to determine the first bend angle along a first axis and the second bend angle along a second axis in a different direction than the first axis. In such an example, the sensor device may comprise a plurality of dielectric layers interleaved with the plurality of electrodes. In such an example, the plurality of dielectric layers may comprise a dielectric coating formed on each of the plurality of electrodes. In such an example, the dielectric coating for each electrode may comprise a polymer/ceramic composite material. In such an example, the first electrode and the second electrode may be positioned on a same side of the reference electrode. In such an example, the first electrode and the second electrode alternatively may be positioned on different sides of the reference electrode.

Another example provides, at a sensor device comprising a plurality of electrodes, a method, comprising receiving a first signal from a first electrode of the plurality of electrodes, a second signal from a second electrode of the plurality of electrodes, and a reference signal from a reference electrode of the plurality of electrodes, outputting a first bend angle of the sensor device for the first joint region based on the first signal and the reference signal, and outputting a second bend angle of the sensor device for the second joint region based on the second signal and the reference signal. In such an example, the method may comprise outputting the first bend angle and the second bend angle to a computing device configured to render a virtual hand model with a pose based on the first bend angle and the second bend angle. In such an example, the computing device may be configured to render a virtual object based on the pose of the virtual hand model. In such an example, the method may alternatively or additionally comprise applying respective correction terms for the first bend angle and the second bend angle, each of the respective correction terms at least partially correcting for one or both of an elongation of the sensor device and a pressure applied to a surface of the sensor device. In such an example, the method alternatively or additionally may comprise comparing the first signal to the second signal to determine a direction in which one or more of the first articulable joint and the second articulable joint is bent. In such an example, the method alternatively or additionally may comprise determining the first bend angle along a first axis and the second bend angle along a second axis perpendicular to the first axis.

Another example provides a wearable device configured to be worn by a user, the wearable device comprising a body, and a sensor device comprising a plurality of electrodes arranged in a stack and connected to a base, the plurality of electrodes comprising a first electrode arranged at a first joint region of the sensor device that is configured to be positioned at a first articulable joint of the user, a second electrode arranged at a second joint region of the sensor device that is configured to be positioned at a second articulable joint of the user, and a reference electrode, and a controller configured to receive a first signal from the first electrode, a second signal from the second electrode, and a reference signal from the reference electrode, output a first bend angle of the sensor device for the first joint region based on the first signal and the reference signal, and output a second bend angle of the sensor device for the second joint region based on the second signal and the reference signal. In such an example, the body may comprise a glove. In such an example, the controller may be configured to apply respective correction terms for the first bend angle and the second bend angle, each of the respective correction terms correcting at least partially for one or both of an elongation of the sensor device and a pressure applied to a surface of the sensor device.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A sensor device configured to span a first articulable joint and a second articulable joint, the sensor device comprising:
    a plurality of electrodes arranged in a stack and connected to a base, the plurality of electrodes comprising a first electrode arranged at a first joint region of the sensor device that is configured to be positioned at the first articulable joint, a second electrode arranged at a second joint region of the sensor device that is configured to be positioned at the second articulable joint, and a reference electrode; and
    a controller configured to
        receive a first signal from the first electrode, a second signal from the second electrode, and a reference signal from the reference electrode;
        determine a first bend angle of the sensor device for the first joint region based on the first signal and the reference signal;
        determine a second bend angle of the sensor device for the second joint region based on the second signal and the reference signal;
        apply respective correction terms for the first bend angle and the second bend angle, each of the respective correction terms correcting at least partially for capacitance changes arising from one or both of an elongation of the sensor device and a pressure applied to a surface of the sensor device; and
        output the first bend angle and the second bend angle.

2. The sensor device of claim 1, wherein the base comprises electrical connectors for connecting the first electrode, the second electrode, and the reference electrode to the controller.

3. The sensor device of claim 1, wherein the controller is further configured to compare the first signal to the second signal and output a determination of a direction in which one or more of the first articulable joint and the second articulable joint is bent.

4. The sensor device of claim 1, wherein the controller is configured to determine the first bend angle along a first axis and the second bend angle along a second axis in a different direction than the first axis.

5. The sensor device of claim 1, further comprising a plurality of dielectric layers interleaved with the plurality of electrodes.

6. The sensor device of claim 5, wherein the plurality of dielectric layers comprises a dielectric coating formed on each of the plurality of electrodes.

7. The sensor device of claim 6, wherein the dielectric coating for each electrode comprises a polymer/ceramic composite material.

8. The sensor device of claim 1, wherein the first electrode and the second electrode are positioned on a same side of the reference electrode.

9. The sensor device of claim 1, wherein the first electrode and the second electrode are positioned on different sides of the reference electrode.

10. At a sensor device comprising a plurality of electrodes, a method, comprising:
    receiving a first signal from a first electrode of the plurality of electrodes, a second signal from a second electrode of the plurality of electrodes, and a reference signal from a reference electrode of the plurality of electrodes;
    determining a first bend angle of the sensor device for the first joint region based on the first signal and the reference signal;
    determining a second bend angle of the sensor device for the second joint region based on the second signal and the reference signal;
    applying respective correction terms for the first bend angle and the second bend angle, each of the respective correction terms correcting at least partially for capacitance changes arising from one or both of an elongation of the sensor device and a pressure applied to a surface of the sensor device; and
    outputting the first bend angle and the second bend angle.

11. The method of claim 10, further comprising outputting the first bend angle and the second bend angle to a computing device configured to render a virtual hand model with a pose based on the first bend angle and the second bend angle.

12. The method of claim 11, wherein the computing device is further configured to render a virtual object based on the pose of the virtual hand model.

13. The method of claim 10, further comprising comparing the first signal to the second signal to determine a direction in which one or more of the first articulable joint and the second articulable joint is bent.

14. The method of claim 10, further comprising determining the first bend angle along a first axis and the second bend angle along a second axis perpendicular to the first axis.

15. A wearable device configured to be worn by a user, the wearable device comprising:
    a body; and
    a sensor device comprising
        a plurality of electrodes arranged in a stack and connected to a base, the plurality of electrodes comprising a first electrode arranged at a first joint region of the sensor device that is configured to be positioned at a first articulable joint of the user, a second electrode arranged at a second joint region of the sensor device that is configured to be positioned at a second articulable joint of the user, and a reference electrode; and
        a controller configured to
            receive a first signal from the first electrode, a second signal from the second electrode, and a reference signal from the reference electrode;
            determine a first bend angle of the sensor device for the first joint region based on the first signal and the reference signal;
            determine a second bend angle of the sensor device for the second joint region based on the second signal and the reference signal;
            apply respective correction terms for the first bend angle and the second bend angle, each of the respective correction terms correcting at least partially for capacitance changes arising from one or both of an elongation of the sensor device and a pressure applied to a surface of the sensor device; and
            output the first bend angle and the second bend angle.

16. The wearable device of claim 15, wherein the body comprises a glove.

\* \* \* \* \*